Figure 1:
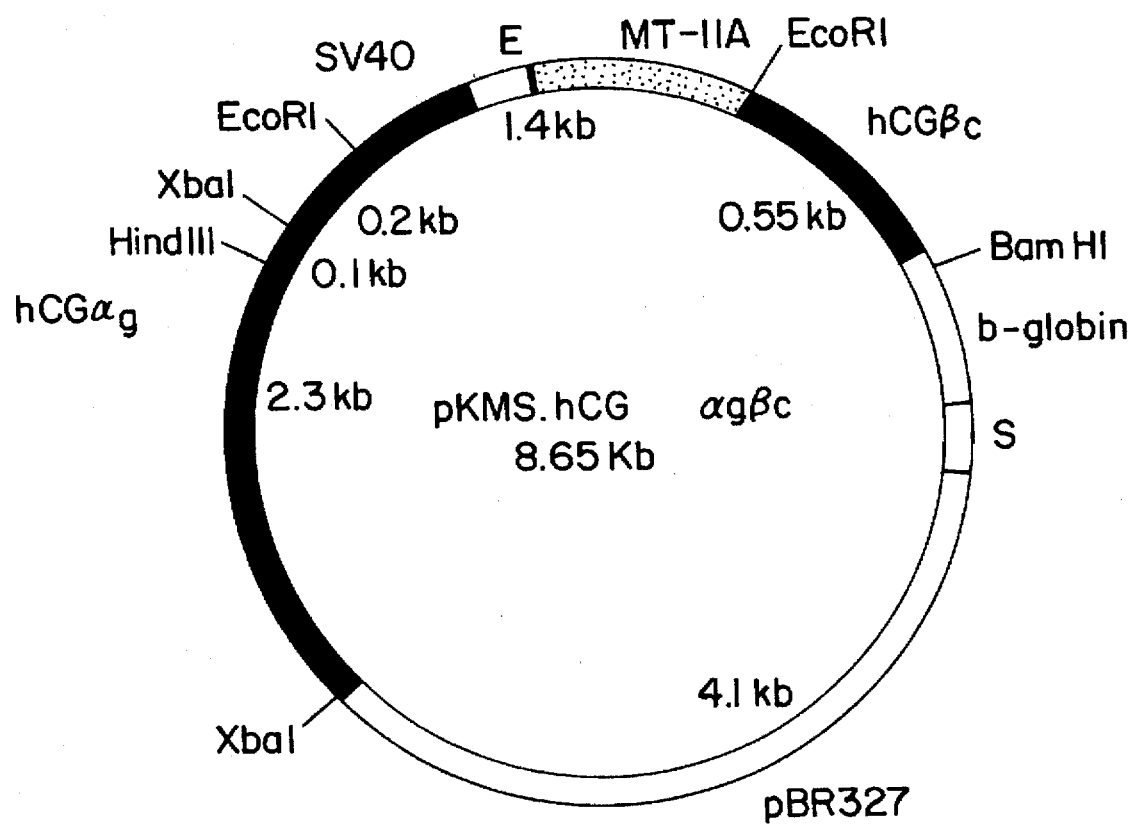

United States Patent [19]
Grootenhuis et al.

[11] Patent Number: 5,691,455
[45] Date of Patent: Nov. 25, 1997

[54] GONADOTROPINS WITH NON-NATIVE DISULFIDE BRIDGES

[75] Inventors: Pieter Diederik Jan Grootenhuis; Judith Christina Heikoop, both of Oss, Netherlands

[73] Assignee: Akzo Nobel N.V., Arnhem, Netherlands

[21] Appl. No.: 556,114

[22] Filed: Nov. 9, 1995

[30] Foreign Application Priority Data

Oct. 24, 1995 [EP] European Pat. Off. ............ 95202876

[51] Int. Cl.$^6$ .................... A61K 38/24; A61K 38/00; C07K 14/59; C07K 14/00
[52] U.S. Cl. .................... 530/398; 530/397; 530/324; 530/850; 514/2; 514/8; 514/12
[58] Field of Search .................... 514/8; 530/398, 530/397

[56] References Cited

PUBLICATIONS

Bedow, E. et al. Kinetics of folding and assembly of the human chorionic gonadotropin b subunit in transfected chinese hamster ovary cells. J. Biol. Chemistry, 267 (13) 8880–8886, 1990.

H. Xia et al., *Journal of Biological Chemistry*, 269:27:17944–17953, 1994.

*Primary Examiner*—Cecilia J. Tsang
*Assistant Examiner*—Michael Borin
*Attorney, Agent, or Firm*—Mary E. Gormley

[57] ABSTRACT

The present invention relates to gonadotropins consisting of an α and β subunit, said gonadotropins comprising non-native disulfide bridges, preferably non-native intersubunit disulfide bridges. The gonadotropins according to the invention have improved stability. The present invention furthermore provides for pharmaceutical compositions comprising said gonadotropins.

20 Claims, 5 Drawing Sheets subunit -

-46

-30

FIG. 2C 1    2    3    M

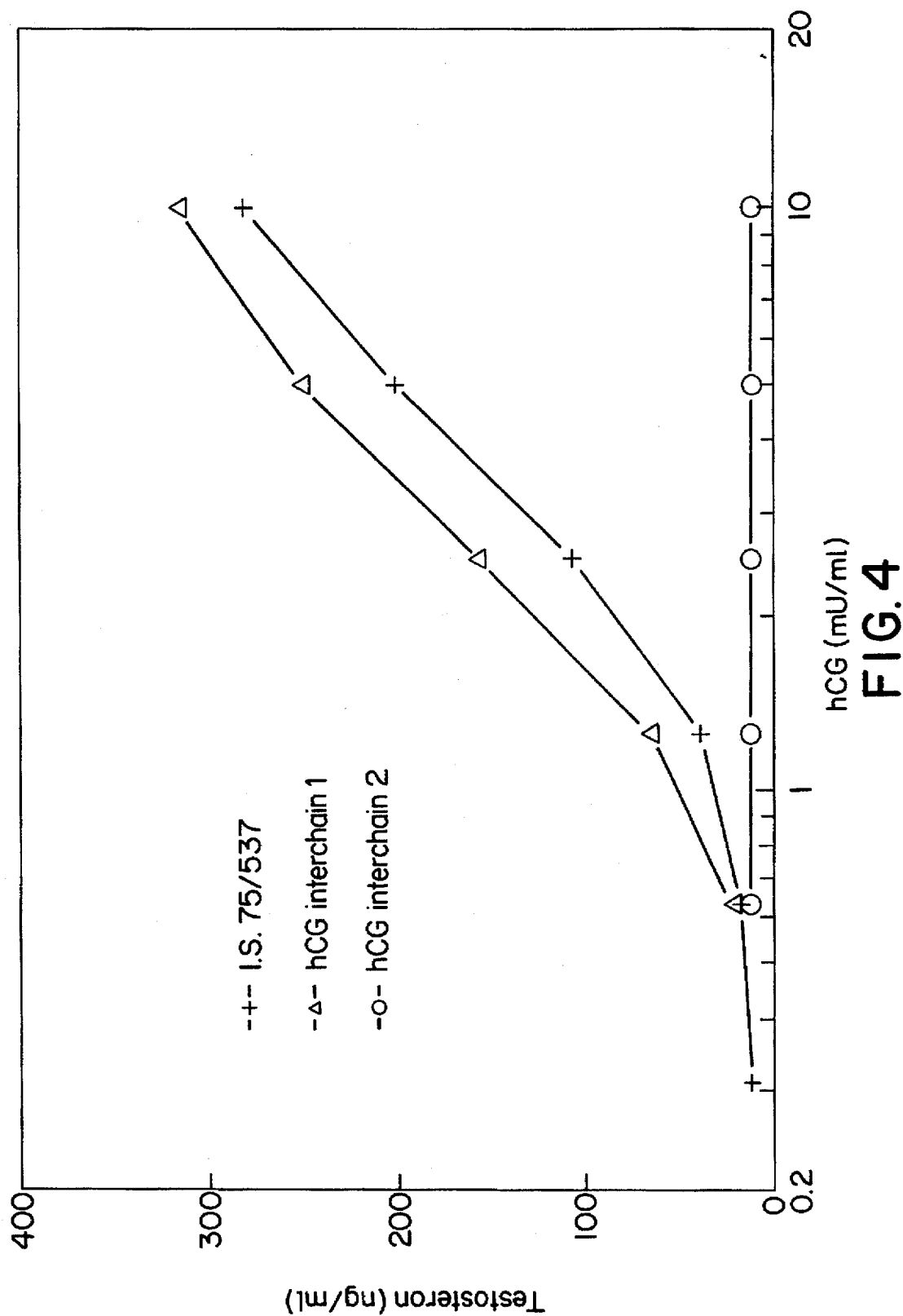

GONADOTROPINS WITH NON-NATIVE DISULFIDE BRIDGES

The invention relates to gonadotropins, pharmaceutical compositions comprising said gonadotropins and DNA encoding said gonadotropins.

The gonadotropins form a family of structurally related glycoprotein hormones. Typical members include chorionic gonadotropin (CG), follicle stimulating hormone (FSH), luteinizing hormone (LH) and thyroid stimulating hormone (TSH). FSH, LH and TSH are present in most vertebrate species and are synthesized and secreted by the pituary. CG has so far been found only in primates, including humans, and in horses and is synthesized by placental tissue.

The gonadotropins are heterodimers composed of two dissimilar subunits, named $\alpha$ and $\beta$, which are associated by non-covalent bonds. Within a species, the $\alpha$-subunit is essentially identical for each member of the gonadotropin family; it also highly conserved from species to species. The $\beta$-subunits are different for each member, i.e. CG, FSH, TSH and LH, but show considerable homology in structure. Furthermore, also the $\beta$ subunits are highly conserved from species to species. In humans, the $\alpha$ subunit consists of 92 amino acid residues, whilst the $\beta$ subunit varies in size for each member: 111 residues in hFSH, 114 residues in hLH, 118 residues in hTSH and 145 residues in hCG (Combarnous, Y. Endocrine Reviews Vol. 13:670–691, 1992; Lustbader, J. W. et al, Endocrine Reviews Vol. 14:291–311, 1993). The $\beta$ subunit of hCG is substantially larger than the other $\beta$ subunits in that it contains approximately 34 additional amino acids at the C-terminus referred to herein as the carboxy terminal protein (CTP).

The two subunits of the heterodimer display many conserved intra-subunit disulfide bonds: five disulfide bridges in the $\alpha$-subunit and six disulfide bridges in the $\beta$-subunit. The corresponding cysteine residues are fully conserved among all members of the gonadotropin family. The recently obtained X-ray structure of hCG shows that these disulfide bonds are involved in typical three dimensional patterns called disulfide knots. The gonadotropins possess three or four asparagine residues that can be N-glycosylated. In addition the C-terminal peptide (CTP) of hCG can be O-glycosylated at four serine positions.

The gonadotropins serve important functions in a variety of bodily functions including: metabolism, temperature regulation and the reproductive process. The hypophyseal gonadotropin FSH for example plays a pivotal role in the stimulation of follicle development and maturation whereas LH induces ovulation (Sharp, R. M. Clin Endocrinol. 33:787–807, 1990; Dorrington and Armstrong, Recent Prog. Horm. Res. 35:301–42, 1979). Currently, FSH is applied clinically, either alone or in combination with LH activity, for ovarian stimulation i.e. ovarian hyperstimulation for in vitro fertilisation (IVF) and induction of in vivo ovulation in infertile anovulatory women (Insler, V., Int. J. Fertility 33:85–97, 1988, Navot and Rosenwaks, J. Vitro Fert. Embryo Transfer 5:3–13, 1988), as well as for male hypogonadism.

At present gonadotropins destined for therapeutic purposes are isolated from human urine sources and are of low purity (Morse et al, Amer. J. Reproduct. Immunol. and Microbiology 17:143, 1988). In contrast to these urinary gonadotropins, recombinant gonadotropins offer great advantages in that they are of constant quality i.e. have reproducible biochemical and biological properties. Genomic and cDNA clones have been prepared for all subunits and their primary structure has been resolved. Moreover, Chinese Hamster Ovary (CHO) cells have been transfected with human gonadotropin subunit genes and these cells are shown to be capable of secreting intact dimers (e.g. Keene et al, J. Biol. Chem. 264:4769–4775, 1989; Van Wezenbeek et al, From clone to Clinic (eds Crommelin D. J. A. and Schellekens H.) pp. 245–251, 1990).

Since then, it has been demonstrated that the biochemical and biological characteristics of e.g. recombinant FSH are almost identical to those of natural FSH (Mannaerts et al, Endocrinology 129:2623–2630, 1991). Moreover, pregnancies were achieved after controlled ovarian superovulation using recombinant FSH (Germond et al, Lancet 339:1170, 1992; Devroey et al, Lancet 339:1170–1171, 1992).

The successful assembly of the two subunits into the dimer is an absolute prerequisite for the biological activity of the dimer. Dissociation of the heterodimer into the corresponding subunits is considered to be a major event in loss of bioactivity in vivo. Furthermore, processes such as dissociation and deamidation lead to an impoverished shelflife. The thermodynamic stability of the heterodimer is therefore considered to be an important factor that affects the half-life of the gonadotropins both under in vivo as well as in vitro conditions. Hence, there is a clinical need for further improvements in the stability of the gonadotropins.

The present invention provides for such gonadotropins. It was suprisingly found that one or more non-native disulfide bridges could be introduced into the gonadotropins resulting in enhanced stability of said gonadotropins. Non-native disulfide bridges as described herein are disulfide bridges that do not occur in the native gonadotropins, hence the non-native disulfide bridges do not encompass the five disulfide bridges in the $\alpha$ subunit nor the six disulfide bridges in the $\beta$ subunit that are present in the native gonadotropins. "Native" gonadotropins are those gonadotropins which have the same amino acid sequence as the gonadotropins isolated from the relevant tissue.

Thus the present invention provides for gonadotropins consisting of an $\alpha$ subunit and a $\beta$ subunit which comprise one or more non-native disulfide bridges.

The non-native disulfide bridges can be introduced by site directed mutagenesis: point mutation of the native amino acid residue at the relevant position into a cysteine. The point mutation is notated as X $\alpha$y Cys or X $\beta$y Cys in which X is the amino acid residue at the relevant position y of the $\alpha$ or $\beta$ subunit, respectively, mutated into cysteine (the three-letter code is used for the amino acids). The point mutations according to the invention lead to subtle changes in the conformation of the gonadotropins.

The non-native disulfide bridges according to the invention can be present between pairs of amino acid residues whereby the amino acid residues are positioned on different subunits (intersubunit). Additionally, the non-native disulfide bridges can also be present between pairs of amino acid residues in which both amino acid residues are positioned on the same subunit (intrasubunit). Optionally, as a result of the presence of one or more of the non-native disulfide bridges according to the invention, one or more of the eleven native disulfide bridges can be deleted.

The non-native disulfides bridges according to the invention prevent dimer dissociation resulting in higher biostabilities and improved shelflife relative to the native glycoproteins. Furthermore, they diminish the flexibility of the polypeptide backbone of the gonadotropins, thus making these gonadotropins less susceptible to deamidation. Deamidation is a spontaneous process that occurs under physiological conditions and which affect the purity and protein stability in a negative way.

Gonadotropins in which a combination of non-native inter- and intrasubunit disulfide bridges are present are also within the scope of the invention.

Suitable gonadotropins according to the invention, in which the α subunit is of human origin, comprise a non-native intrasubunit disulfide bridge between one or more of the amino acid pairs (Phe α18 Cys-Ileα25 Cys), (Gln α20 Cys-Ala α23 Cys), (Ser α34 Cys-Ser α57 Cys), (Thr α39 Cys-Thr α54 Cys), (Ala α62 Cys-His α79 Cys), and (Lys α63 Cys-Ala α81 Cys), (Tyr α65 Cys-His α79 Cys), and (Asn α66 Cys-Asn α78 Cys).

Suitable gonadotropins according to the present invention, in which the β subunit is the β subunit of hCG, can comprise an intersubunit disulfide bridge between one or more of the amino acid pairs (Gln α5 Cys-Arg β8 Cys), (Pro α24 Cys-Gly β71 Cys), (Met α29 Cys-Met β41 Cys), (Arg α35 Cys-Ala β35 Cys), (Tyr α37 Cys-Ile β33 Cys), and (Lys α51 Cys-Asp β99 Cys) and/or an intrasubunit disulfide bridge between one or more of the amino acid pairs (Pro β4 Cys-Pro β7 Cys), (Pro β11 Cys-Thr β32 Cys), (Pro β11 Cys-Ala β85 Cys), (Thr β32 Cys-Ala β85 Cys), (Arg β60 Cys-Ser β87 Cys), (Arg β60 Cys-Gln β89 Cys), (Asp β61 Cys-Leu β86 Cys), (Asp β61 Cys-Ser β87 Cys), (Ser β66 Cys-Ser β81 Cys) and (Leu β69 Cys-Pro β78 Cys). Preferably, the hCG according to the invention comprise a non-native, intersubunit disulfide bridge between the amino acid pairs (Met α29 Cys-Met β41 Cys), (Tyr α37 Cys-Ile β33 Cys), or (Lys α51 Cys-Aspβ99 Cys).

Suitable gonadotropins according to the invention, in which the β subunit is the β subunit of hLH, comprise an intersubunit disulfide bridge between one or more of the amino acid pairs (Gln α5 Cys-Trp β8 Cys), (Pro α24 Cys-Gly β71 Cys), (Met α29 Cys-Met β41 Cys), (Arg α35 Cys-Ala β35 Cys), (Tyr α37 Cys-Ile β33 Cys) and (Lys α51 Cys-Asp β99 Cys) and/or an intrasubunit disulfide bridge between one or more of the amino acid pairs (Pro β4 Cys-Pro β7 Cys), (Pro β11 Cys-Thr β32 Cys), (Pro β11 Cys-Ala β85 Cys), (Thr β32 Cys-Ala β85 Cys), (Arg β60 Cys-Ser β87 Cys), (Arg β60 Cys-Arg β89 Cys), (Asp β61 Cys-Leu β86 Cys), (Asp β61 Cys-). Ser β87 Cys), (Ser β66 Cys-Ser β81 Cys) and (Leu β69 Cys-Pro β78 Cys).). A preferred gonadotropin according to the invention is hLH comprising a disulfide bridge between the amino acid pairs (Met α29 Cys-Met β41 Cys), (Tyr α37 Cys-Ile β33 Cys), or (Lys α51 Cys-Asp β99 Cys).

Suitable gonadotropins according to the invention, in which the β subunit is the β subunit of hFSH, comprise an intersubunit disulfide bridge between one or more of the amino acid pairs (Gln α5 Cys-Ser β2 Cys), (Pro α24 Cys-Gly β65 Cys), (Met α29 Cys-Arg β35 Cys), (Arg α35 Cys-Ala β29 Cys), (Tyr α37 Cys-Trp β27 Cys) and (Lys α51 Cys-Asp β93 Cys) and/or an intrasubunit disulfide bridge between one or more of the amino acid pairs (Leu β5 Cys-Thr β26 Cys), (Leu β5 Cys-Ala β79 Cys), (Thr β26 Cys-Ala β79 Cys), (Lys β54 Cys-Gln β81 Cys), (Lys β54 Cys-His β83 Cys), (Glu β55 Cys-Thr β80 Cys), (Glu β55 Cys-Gln β81 Cys), (Thr β60 Cys-Thr β75 Cys) and (Val β63 Cys-Ser β72 Cys). A preferred gonadotropin according to the invention is hFSH in which the β subunit comprises an intersubunit disulfide bridge between the amino acid pair (Tyr α37 Cys-Trp β27 Cys).

Suitable gonadotropins according to the invention, in which the β subunit is the β subunit of hTSH, comprise an intersubunit disulfide bridge between one or more of the amino acid pairs (Gln α5 Cys-Phe β1 Cys), (Pro α24 Cys-Gly β66 Cys), (Met α29 Cys-Arg β34 Cys), (Arg α35 Cys-Ala β28 Cys), (Tyr α37 Cys-Ile β26 Cys) and (Lys α51 Cys-Asp β94 Cys) and/or an intrasubunit disulfide bridge between one or more of the amino acid pairs (Pro β4 Cys-Thr β25 Cys), (Pro β4 Cys-Ala β80 Cys), (Thr β25 Cys-Ala β80 Cys), (Arg β55 Cys-Ser β82 Cys), (Arg β55 Cys-Lys β84 Cys), (Asp β56 Cys-Leu β81 Cys), (Asp β56 Cys-Ser β82 Cys), (Thr β61 Cys-Ser β76 Cys) and (Ile β64 Cys-Pro β73 Cys).

The mutation positions as presented above relate to the amino acid sequence of the human gonadotropins. Comparable non-native disulfide bridges within the subunits of the gonadotropins from other species are also within the scope of the invention. The exact position of the amino acid residues to be mutated into a cysteine can be derived from sequence alignment of said gonadotropin subunits with the human gonadotropin subunits.

Because of the major role that the disulfide bonding plays during the subunit folding and assembly, it is very surprising that the introduction of the non-native disulfide bridges according to the invention does not interfere with the formation of properly folded gonadotropins. Proper disulfide bond formation is a critical event in the folding and maturation of functional gonadotropins. Especially the disulfide bond formation in the β subunit is critical: all disulfide bonds are required for efficient combination and folding. Detailed studies of the folding of hCG revealed that the folding of the molecule does not proceed by a simple sequential pathway, but proceeds independently in different domains of the molecule. It was therefore thought that the introduction of additional cysteine residues in the α and/or β subunits would disturb the folding process resulting in a loss of conformation of the molecule and as a consequence thereof loss of functionality and bioactivity of the molecule. Especially, since so many cysteines are already present in these molecules.

The point mutations into cysteines according to the invention only marginally change the overall amino acid composition and protein characteristics, thus the gonadotropins according to the invention have the additional advantage that their potential immunogenecity will not differ substantially from the immunogenecity of the wild type gonadotropins. Especially, when the non-native disulfide bridges are positioned at the dimer interface of the gonadotropins, the effect on the immunogenecity will be neglectable.

The gonadotropins according to the invention can be agonists or antagonists, depending on the mutation site. As already mentioned before, the mutation site may lead to subtle changes in the conformation of the molecule. If the mutation site is selected in parts of the protein that are associated with receptor binding and/or signal transduction, the non-native disulfide bridges according to the invention may lead to a partial or complete loss of signal transduction activity in combination with enhanced glycoprotein stability's. Thus the present invention provides for antagonists with enhanced stability's. If the mutation site is selected at the dimer interface of the inner core of the glycoprotein, the resulting non-native disulfide bridges will not effect the receptor binding and/or signal tranduction activity, but will lead to enhanced stability's relative to the native gonadotropins. Such mutations will result in gonadotropin agonists with enhanced stability's.

The gonadotropins according the invention can comprise other modification generally known in the art.

In one such preferred modification of the gonadotropins according to the invention, the C-terminus of the amino acid sequence of one of the subunits is linked, optionally through a linker moiety, to the N-terminus of the amino acid sequence of the other subunit. Preferably the linker moiety is a complete or partial CTP unit or variant thereof.

Another modification of the gonadotropins according to the invention can be an extension of the α and/or β subunit at their respective N- or C-terminus with a complete or partial CTP unit or a variant thereof. The extension may comprise the respective CTP units in single or multiple forms. Alternatively, a complete CTP unit or partial CTP unit or multiple forms thereof can be inserted in the N- or C-terminus of said subunits.

Furthermore, the gonadotropins according to the invention may be either glycosylated, partially glycosylated or non-glycosylated. Partially or non-glycosylated gonadotropins according to the invention can be obtained either through chemical modification, enzymatic modification or by site-directed mutagenesis whereby one or more of the glycosylation recognition sites in the gonadotropins are removed. Alternatively, the glycosylation pattern of the gonadotropins according to the invention can be modified by the introduction of additional glycosylation recognition sites and, optionally, the removal of one or more glycosylation recognition sites, resulting in a modified glycosylation of said gonadotropins. A glycosylation recognition site as used herein consists of the amino acid sequence Asn-X-Ser/Thr, wherein X can be any amino acid.

As used herein the α and β subunits of CG, FSH, LH and TSH as well as the heterodimeric forms have in general their conventional defenitions and refer to the proteins having the amino acid sequences known in the art per se, or allelic variants thereof, regardless of the glycosylation pattern displayed.

"Native" forms of these proteins are those proteins which have the amino acid sequences as isolated from the relevant vertebrate tissue, and have these known sequences per se, or their allelic variants thereof.

These "variants" are those proteins which have deliberate alterations in amino acid sequences relative to the native proteins. The alterations my include single or multiple deletions, insertions, substitutions and combinations thereof, and can be produced by, for example, site specific mutagenesis or by other recombinant manipulations, or can be prepared synthetically. Preferably these alterations consist of conservative amino acid substitutions, in which the residue substituted is of the same general amino acid category as that for which substitution is made. Such classification of the amino acids is generally known in the art and described by, for example, Dayhoff, M. et al, Atlas of Protein Sequences and Structure 5:89–99 (1972).

As used herein, the "CTP unit" refers to the amino acid sequence found at the carboxy terminus of the β subunit of hCG which extends from amino acid 112–118 to residue 145 at the C-terminus or to a portion thereof. A "complete" CTP unit contains 28–34 amino acids, depending on the N-terminus of the CTP. A "partial" CTP unit is an amino acid sequence which occurs between positions 112–118 to 145 inclusive, but which has at least one amino acid deleted from the shortest possible complete CTP unit (amino acid 118–145). "Multiple" CTP units are understood to encompass tandem arrays of the complete CTP unit or partial CTP unit or combinations of both.

DNA encoding any of the gonadotropins according to the invention are also within the scope of the invention. Said DNA according to the invention comprises one or more cysteine-encoding codons which have been substituted for the codons that encode the amino acid to be replaced. DNA according to the invention can be obtained from the DNA encoding the native gonadotropins or variants thereof by the substitution in said DNA of one or more codons encoding the amino acid residue that is to be replaced with a cysteine encoding codon. These substitutions can be performed by site-directed mutagenesis.

Methods to construct the gonadotropins according to the invention are well known in the art (Sambrook et al., Molecular Cloning: a Laboratory Manual, Cold Spring Harbor Laboratory Press, Cold Spring Harbor, latest edition). The most practical approach is to produce these gonadotropins by expression of the DNA encoding the desired protein. Techniques for site directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eucaryotic hosts such as yeast, plant cells, insect cells, mammalian cells, avian cells and the like. The choice of host is particularly to post-translational events, most particularly including glycosylation. The location of glycosylation is mostly controlled by the nature of the glycosylation site within the molecule. However, the nature of the sugars occupying this site is largely controlled by the nature of the host.

The gonadotropins according to the invention can be used for the same clinical purposes as the native gonadotropins, with the advantage that they display an improved stability. Suitable pharmaceutical compositions according to the invention comprise one or more of the gonadotropins according to the invention and a pharmaceutical acceptable carrier. Very suitable to be used in a pharmaceutical composition according to the invention are gonadotropins according to the invention which comprise Pharmaceutical acceptable carders are well known to those skilled in the art and include, for example, sterile salin, lactose, sucrose, calcium phosphate, gelatin, dextrin, agar, pectin, peanut oil, olive oil, sesame oil and water.

Furthermore the pharmaceutical composition according to the invention may comprise one or more stabilizers such as, for example, carbohydrates including sorbitol, mannitol, starch, sucrosedextrin and glucose, proteins such as albumin or casein, and buffers like alkaline phosphates.

Suitable administration routes are intramuscular injections, subcutaneous injections, intravenous injections or intraperitoneal rejections, oral and intranasal administration.

The following examples are illustrative for the invention and should in no way be interpreted as limiting the scope of the invention.

LEGENDS TO THE FIGURES

FIG. 1: Structural organisation of hCGα$_g$β$_c$ expression plasmid pMKS.hCGα$_c$β$_c$. SV40=Sv40 early promoter. E=M-MuLV enhancer. MT-II$_A$=human metallothionein-II$_A$ promoter. hCGα$_g$=genomic hCGα mini gene coding for hCGα subunit. hCGβ$_c$=cDNA coding for hCGβ subunit. β-globin=rabbit β-globin polyadenylation sequence and splice signals. S=SV40 transcription termination sequence. pBR327=part of plasmid pBR327 containing E. coli origin of replication and amicillin resistance gene.

Figure 2A:
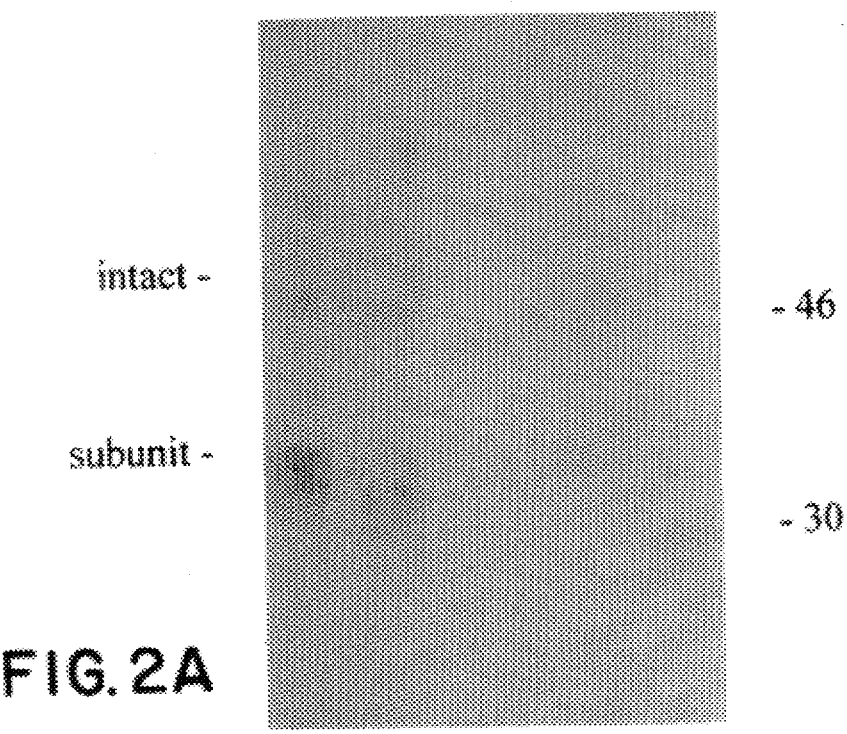
Figure 2B:
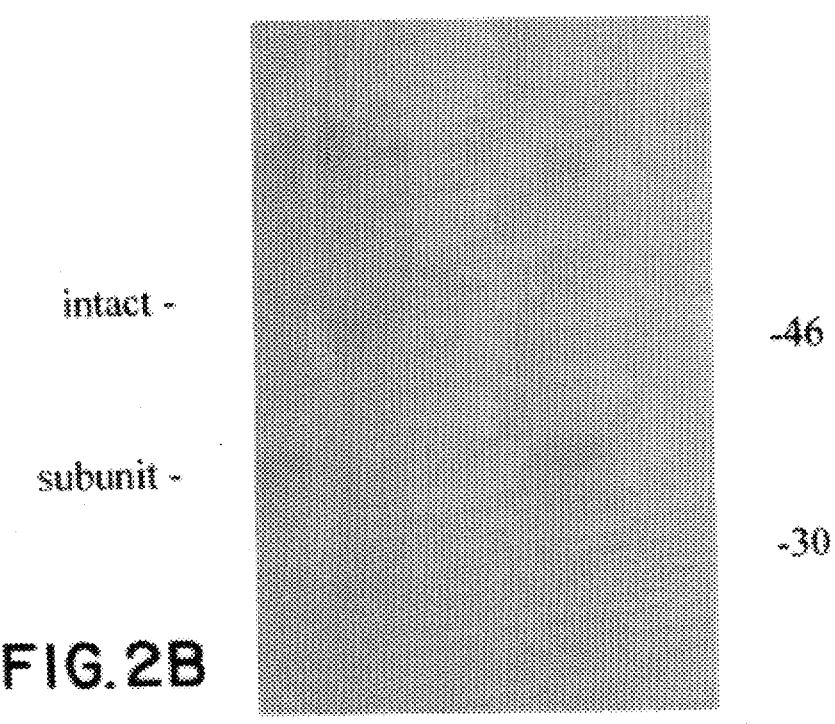
Figure 2C:
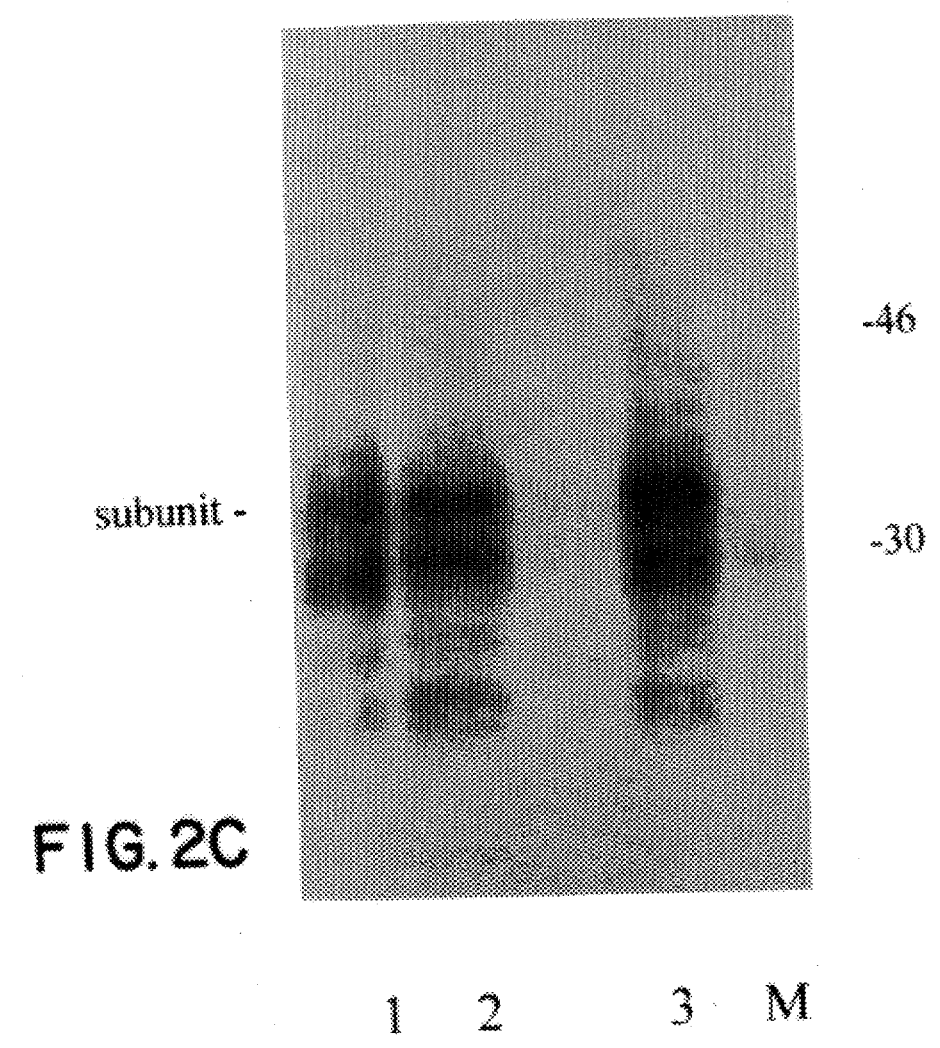

FIG. 2: Western blot analysis of cell culture supernatants from hCG interchain 1, hCG interchain 2 and hCG wild type for the expression of hCG (muteins) and formation of intersubunit disulfide bridges. Cell culture supernatants from G418-resistant transfection pools hCG interchain 1, hCG interchain 2 and from rec-hCG wild type containing approx. 0.2 IU hCG were solubilised at room temperature (Panel A) or 100° C. (Panels B and C) in SDS-containing sample buffer in the absence (Panels A and B) or presence of β-mercapto ethanol (Panel C). Following electrophoresis and transfer to PVDF membranes hCG was visualised by incubation with a β-hCG specific monoclonal antibody followed by incubation with a second antibody-HRP conjugate and staining with TMB. As can be seen solubilisation as room temperature (Panel A, lanes 1 and 2) and 100° C. (Panel B lanes 1 and 2) both remit in the detection of intact hormone whereas in the control (WT-hCG) boiling dissociates the hormone into its subunits (Panel B lane 3). Addition of reducing agent results in the dissociation into subunits in all three samples (Panel C). The combined data thus lead to the conclusion that both HCG interchain 1 and 2 are stabilised by a intermolecular disulfide bridge.

Figure 3:
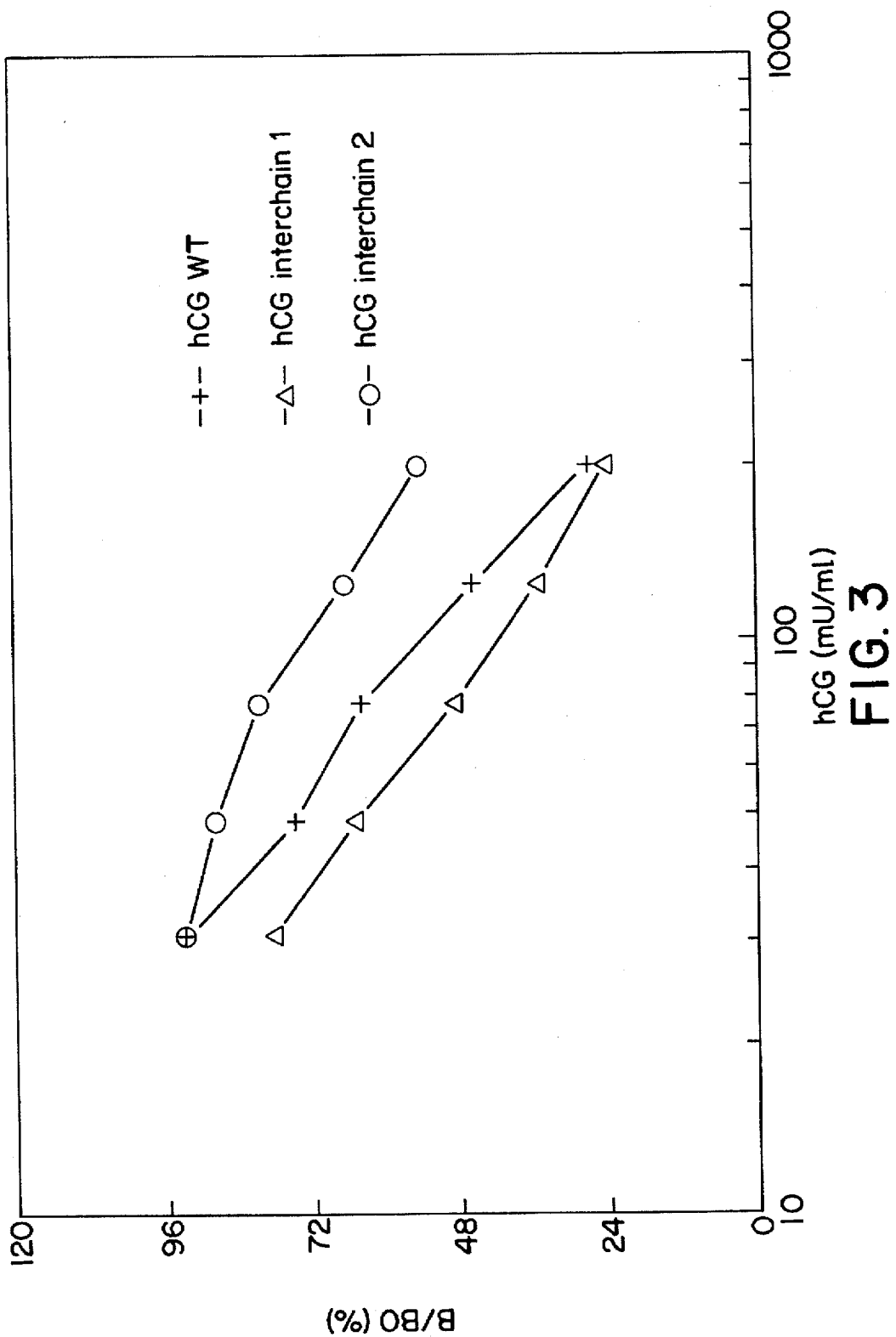

FIG. 3: hCG displacement assay of hCG intersubunit muteins. $B/B_0$=% of total binding . . . -+-=hCG wild type (WT) - -=hCG interchain 1. -0=hCG interchain 2.

FIG. 4: In vitro bioactivity of hCG intersubunit muteins. -+- =LS 75/537. - -=hCG interchain 1. -0-=hCG interchain 2.

EXAMPLES

Example 1

Production interchain muteins
Vector construction

Three constructs were generated to express hCG muteines containing an additional interchain disulfide bond. Their structure and overall organisation is essentially identical to that of pKMS.hCCα$_g$β$_c$, the vector used for the expression of recombinant wild-type hCG in CHO cells (FIG. 1). The respective hCG α and β subunit genes have been inserted in pKMS. By combining a cDNA with a genomic clone a complete 'hybrid' hCGα gene has been prepared (a) capable of expressing wild type α subunit upon transfection in a host cell. cDNA for hCGβ was isolated as described (c) and exchanged with FSHβ in the vector pKMS.FSH (a). Transcription of the α gene is directed from the SV40 early promoter whereas the β gene is transcribed from the human heavy metal inducible metallothionein IIa promoter. Three hCG interchain constructs were made (Table 1).

For the construction of the α subunit mutation in hCG-interchain 1, specific base substitutions were introduced in the 'hybrid' hCGα gene in such a way that the codon encoding tyrosine α37 was changed in a codon encoding cysteine. This was performed by site-specific mutagenesis and combining PCR fragments that overlap in sequences as described (d), using standard PCR conditions. The PCR-fragments were separated, subcloned in pGEM3Z and checked using an Automated sequencer (Pharmacia). The primers were chosen in such a way that the subcloned PCR-fragment contained appropriate restriction-sites both 3' and 5' of the mutation(s) so that it could be exchanged with the native α chain sequence in pKMS.hCGαgβc. This was performed using standard techniques.

For the construction of the β subunit mutation in hCG-interchain 1, specific base substitutions were introduced in the hCGβ in such a way that the codon encoding isoleucine β33 was changed in a codon encoding cysteine. Mutagenic PCR reactions, subcloning and sequencing were performed using methods comparable to the ones used for the construction of the α subunit mutation. For the construction of the final expression plasmid of hCG interchain 1, the hCGβc wild type gene was exchanged with the mutated hCG β-fragment in the pKMS.hCGα$_g$β$_c$ construct which already contained the α subunit mutation.

For the construction of the vectors encoding hCG-interchain 2 (in which the codons encoding lysine α51 and asparagine β have been substituted with cysteine encoding codons) and hCG-interchain 3 (in which the codons encoding methionine α29 and methionine β41 have been substituted with cysteine encoding codons) a comparable strategy was followed.

TABLE 1

| The mutated cysteine codons in hCG. | |
|---|---|
| hCG muteins | codon |
| hCG interchain 1 | Tyr α37 Cys - Ile β33 Cys |
| hCG interchain 2 | Lys α51 Cys - Asp β99 Cys |
| hCG interchain 3 | Met α29 Cys - Met β41 Cys |

Transfection and selection of CHO-cells

CHO K1 cells (ATCC CCL61) were stably transfected with 10 μg of the pKMS.hCG-interchain constructs using Transfectam reagent (Promega). A selection plasmid containing the neomycine selection gene was co-transfected in a molar ratio of 10:1 (excess pKMS hCG-interchain) allowing selection of cells in culture medium containing G418 (0.8 mg/ml).

Recombinant CHO cells were selected for excretion of an immunoreactive protein. Culture supernatants reacted positive in a hCG sandwich ELISA assay using α and β specific monoclonal antibodies. Western blotting of culture supernatant showed that the hCG-interchain muteins have a molecular weight size comparable to that of rec-hCG wild type.

(a) Van Weezenbeek, P., Draaijer, J, Van Meel, F. and Olijve, W. (1990) 'Recombinant Follicle Stimulating Hormone: Construction, Selection and Characterization of a cell line'. In: From Clone to Clinic. D. J. A. Crommelin and H. Schellekens (eds.), 245–251.

(b) Fiddes, J. C. and Goodman, H. M. (1981) 'The genes encoding the common alpha subunit of the four human glycoprotein hormones', J. Mol. Appl. Genet. 1, 3–18.

(c) Fiddes, J. C. and Goodman, H. M. (1980) Nature 286, 684–687.

(d) Erich, H. A. (1989) PCR Technology; Principles and Applications for DNA amplification. Stockton Press, New-York, pp 63–66.

Example 2

Analysis of intersubunit disulfide formation

In order to determine whether the newly introduced cysteines had oxidised into an intersubunit disulfide bond, samples from cell culture supernatants from G418-resistant transfection pools were dissolved by boiling in SDS-containing sample buffer, subjected to SDS-polyacrylamide gel electrophoresis and transferred to a PVDF membrane. hCG was visualised using immunostaining with a monoclonal antibody directed against the β subunit followed by incubation with a second antibody conjugated to horse radish peroxidase (HRP) and staining with tetramethyl benzidine (TMB)/$Co^{++}/H_2O_2$. When an intersubunit disulfide bond had formed, boiling of samples in SDS-sample buffer would keep the two subunits together whereas these solubilisation conditions would cause dissociation into subunits in case no disulphide bridge was formed. In control experiments samples were solubilised without reducing agent at room temperature (intact hCG) and by addition of β-mercapto ethanol (βME). In the latter case denaturation into subunits will occur, irrespective of the presence of interchain disulfide bond. As can be seen in FIG. 2, panel A, solubilisation at room temperature in the absence of βME results in detection of intact wild type hCG (lane 3, molecular mass approx. 50 kD) as well as some free β subunit (mol. mass approx. 32 kD). Samples from HCG interchain 1 and HCG interchain 2 also contain immuno reactive material at approx. the same sizes indicating the presence of intact hCG muteine. Upon heating wild type hCG dissociates into subunits as evidenced by the disappearance of the 50 kD band (panel B lane 3). In contrast, this does not appear to happen with the hCG mutants (panel B, lanes 1 and 2) indicating the presence of intermolecular, covalent bonding. Addition of βME finally demonstrates that intermolecular bonding between the 2 subunits is brought about by a disulfide since addition of reducing agent dissociates hCG and mutants into subunits (panel C).

Example 3

LH/CG-receptor binding

Binding to the LH/CG receptor is the first event in the mechanism of action of hCG. An in vitro receptor assay was used to determine the relative receptor binding potency of hCG interchain muteins by means of displacement of iodinated hCG to rat testis membranes (Rao et al., 1977). For this purpose a fixed amount of [125I]hCG was incubated with rat testis membranes and increasing amounts of sample at room temperature for 18 h. Additional incubations without sample were performed for the assessment of maximal binding. Non-specific binding was determined by adding a 1000 fold excess of unlabeled ligand (Pregnyl, Organon, West Orange, N.J.). Incubation was terminated by diluting the samples 2-fold with ice-cold Tris buffer supplemented with 0.1% BSA and centrifugation at room temperature for 5 rain at 150.000×N.kg-1. After aspiration of the supernatant, radioactivity in the pellet was determined using a gamma counter.

The hCG interchain 1 shows a displacement curve of iodinated hCG comparable to rec-hCG wild type. This demonstrates that the intersubunit disulphide bond of hCG interchain 1 has no effect on receptor binding, indicating that the conformation of this mutein is indeed comparable to the rec-hCG wild type. The displacement of iodinated hCG by hCG interchain 2 is slightly diminished. This is presumably due to the fact that this interchain disulphide bridge is located in an area which is important for receptor binding and signal transaction.

Example 4 hCG-induced testosterone production hCG induces testosterone production in mouse Leydig cells. An in vitro assay (Van Damme et al., 1974 modified by Mannaerts et al., 1987) is used to determine the hCG bioactivity of the hCG muteins containing the interchain disulphide bonds (FIG. 4). Treatment of cells with hCG interchain 1 resulted in dose-dependent increases in testosterone production, with the same potency as rec-hCG wild type. Therefore, hCG interchain 1 can be regarded as a full hCG agonist. In contrast, the signal transducing ability of hCG interchain 2 was reduced to zero, indicating that hCG interchain 2 can be used as a full antagonist of the wild-type hCG.

Rao, M. C., Richards, J. S., Midgley, A. R. Jr, Reichert, L. E. Jr. Endocrinology 101:512–523.

Van Damme, M. P., Robertsen, D. M. and Diczfalusy, E., Acta Endocrinol. (1974) 77:655–671.

Mannaerts, B. M. J. L., Kloosterboer, J. H. and Schuurs, A. H. W. M. (1987), Neuroendocrinology of reproduction, R. Rolland et al. (eds.), Elsevier Science Publishers B. V., 49–58.

We claim:

1. A gonadotropin consisting of an α subunit and a β subunit, wherein said gonadotropin comprises one or more non-native disulfide bridges.

2. A gonadotropin according to claim 1, wherein the non-native disulfide bridges are intersubunit disulfide bridges.

3. A gonadotropin according to claim 1, wherein said gonadotropin comprises a non-native disulfide bridge between one or more of the amino acid pairs (Phe α18 Cys-Ile α25 Cys), (Gln α20 Cys-Ala α23 Cys), (Ser α34 Cys-Ser α57 Cys), (Thr α39 Cys-Thr α54 Cys), (Ala α62 Cys-His α79 Cys), (Lys α63 Cys-Ala α81 Cys), (Tyr α65 Cys-His α79 Cys), and (Asn α66 Cys-Asn α78 Cys).

4. A gonadotropin according to claim 1, wherein the β subunit is the β subunit of hCG.

5. A gonadotropin according to claim 4, wherein said gonadotropin contains a non-native intersubunit disulfide bridge between one or more of the amino acid pairs (Gln α5 Cys-Arg β8 Cys), (Pro α24 Cys-Gly β71 Cys), (Met α29 Cys-Met β41 Cys), (Arg α35 Cys-Ala β35 Cys), (Tyr α37 Cys-Ile β33 Cys), and (Lys α51 Cys-Asp β99 Cys).

6. A gonadotropin according to claim 4, wherein said gonadotropin comprises a non-native disulfide bridge between one or more of the amino acid pairs (Pro β4 Cys-Pro β7 Cys), (Pro β11 Cys-Thr β32 Cys), (Pro β11 Cys-Ala β85 Cys), (Thr β32 Cys-Ala β85 Cys), (Arg β60 Cys-Ser β87 Cys), (Arg β60 Cys-Gln β89 Cys), (Asp β61 Cys-Leu β86 Cys), (Asp β61 Cys-Ser β87 Cys), (Ser β66 Cys-Ser β81 Cys) and (Leu β69 Cys-Pro β78 Cys).

7. A gonadotropin according to claim 1, wherein the β subunit is the β subunit of LH.

8. A gonadotropin according to claim 7, wherein said gonadotropin comprises a non-native intersubunit disulfide bridge between one or more of the amino acid pairs (Gln α5 Cys-Trp β8 Cys), (Pro α24 Cys-Gly β71 Cys), (Met α29 Cys-Met β41 Cys), (Arg α35 Cys-Ala β35 Cys), (Tyr α37 Cys-Ile β33 Cys) and (Lys α51 Cys-Asp β99 Cys).

9. A gonadotropin according to claim 7, wherein said gonadotropin comprises a non-native disulfide bridge between one or more of the amino acid pairs (Pro β4 Cys-Pro β7 Cys), (Pro β11 Cys-Thr β32 Cys), (Pro β11 Cys-Ala β85 Cys), (Thr β32 Cys-Ala β85 Cys), (Arg β60 Cys-Ser β87 Cys), (Arg β60 Cys-Arg β89 Cys), (Asp β61 Cys-Leu β86 Cys), (Asp β61 Cys-Ser β87 Cys), (Ser β66 Cys-Ser β81 Cys) and (Leu β69 Cys-Pro β78 Cys).

10. A gonadotropin according to claim 1, wherein the β subunit is the β subunit of FSH.

11. A gonadotropin according to claim 10, wherein said gonadotropin comprises a non-native intersubunit disulfide bridge between one or more of the amino acid pairs (Gln α5 Cys-Ser β2 Cys), (Pro α24 Cys-Gly β65 Cys), (Met α29 Cys-Arg β35 Cys), (Arg α35 Cys-Ala β29 Cys), (Tyr α37 Cys-Trp β27 Cys) and (Lys α51 Cys-Asp β93 Cys).

12. A gonadotropin according to claim 10, wherein said gonadotropin comprises a non-native disulfide bridge between one or more of the amino acid pairs (Leu β5 Cys-Thr β26 Cys), (Leu β5 Cys-Ala β79 Cys), (Thr β26 Cys-Ala β79 Cys), (Lys β54 Cys-Gln β81 Cys), (Lys β54 Cys-His β83 Cys), (Glu β55 Cys-Thr β80 Cys), (Glu β55 Cys-Gln β81 Cys), (Thr β60 Cys-Thr β75 Cys) and (Val β63 Cys-Ser β72 Cys).

13. A gonadotropin according to claim 1, wherein the β subunit is the β subunit of TSH.

14. A gonadotropin according to claim 13, wherein said gonadotropin comprises a non-native intersubunit disulfide bridge between one or more of the amino acid pairs (Gln α5 Cys-Phe β1 Cys), (Pro α24 Cys-Gly β66 Cys), (Met α29 Cys-Arg β34 Cys), (Arg α35 Cys-Ala β28 Cys), (Tyr α37 Cys-Ile β26 Cys) and (Lys α51 Cys-Asp β94 Cys).

15. A gonadotropin according to claim 13, wherein said gonadotropin comprises a non-native disulfide bridge between one or more of the amino acid pairs (Pro β4 Cys-Thr β25 Cys), (Pro β4 Cys-Ala β80 Cys), (Thr β25 Cys-Ala β80 Cys), (Arg β55 Cys-Ser β82 Cys), (Arg β55 Cys-Lys β84 Cys), (Asp β56 Cys-Leu β81 Cys), (Asp β56 Cys-Ser β82 Cys), (Thr β61 Cys-Ser β76 Cys) and (Ile β64 Cys-Pro β73 Cys).

16. A composition comprising a gonadotropin according to claim 1 and a pharmaceutically acceptable carrier.

17. A composition comprising a gonadotropin according to claim 4 and a pharmaceutically acceptable carrier.

18. A composition comprising a gonadotropin according to claim 7 and a pharmaceutically acceptable carrier.

19. A composition comprising a gonadotropin according to claim 10 and a pharmaceutically acceptable carrier.

20. A composition comprising a gonadotropin according to claim 13 and a pharmaceutically acceptable carrier.

* * * * *

Adverse Decisions in Interference

Patent No. 5,691,455, Peter D.J. Grootenhuis and Judith C. Heikoop, GONADOTROPINS WITH NON-NATIVE DISULFIDE BRIDGES, Interference No. 105,600, final judgment adverse to the patentees rendered December 10, 2009, as to claims 1-20.

(*Official Gazette*, *July 27, 2010*)